United States Patent [19]

Haverstock

[11] Patent Number: 4,976,726
[45] Date of Patent: Dec. 11, 1990

[54] SKIN CLOSURE DEVICES

[76] Inventor: Charles B. Haverstock, 44 Frederick La., Glendale, Mo. 63122

[21] Appl. No.: 343,725

[22] Filed: Apr. 27, 1989

[51] Int. Cl.⁵ .................. A61B 17/00; A61L 13/00
[52] U.S. Cl. .................................. 606/216; 606/213
[58] Field of Search ............... 128/155, 156, 335; 606/215, 216

[56] References Cited

U.S. PATENT DOCUMENTS

| | | | |
|---|---|---|---|
| 2,387,131 | 10/1945 | Fernandez | 128/335 |
| 3,402,716 | 9/1968 | Baxter | 128/335 |
| 3,520,306 | 7/1970 | Gardner et al. | 128/335 |
| 4,230,105 | 10/1980 | Harwood | 128/156 |
| 4,307,717 | 12/1981 | Hymes et al. | 128/156 |
| 4,423,731 | 1/1984 | Roomi | 128/335 |
| 4,531,521 | 7/1985 | Haverstock | 128/335 |
| 4,742,826 | 5/1988 | McLorg | 128/335 |
| 4,788,146 | 11/1988 | Ring et al. | 128/156 |

FOREIGN PATENT DOCUMENTS 445412   5/1975   U.S.S.R. ........................ 606/216

*Primary Examiner*—Randall L. Green
*Assistant Examiner*—Gary Jackson
*Attorney, Agent, or Firm*—Haverstock, Garrett & Roberts

[57] ABSTRACT

Improvements to skin closure devices wherein a sheet member is adhesively attached to the skin and has side edges that extend along and are contiguous with the side edges of the skin opening to be closed, which device also includes bridging members attached to the sheet member on opposite sides of the skin opening for holding portions of the sheet member on opposite sides of the skin opening and the skin opening together in a closed condition, the improvements including an elongated strip of relatively porous material intended to hold a quantity of medication therein substantially along th length thereof, and a layer of adhesive along the length on one surface of the strip for attaching the strip to the skin closure in position extending along the closed skin opening, whereby the medication substance can drain into the medicate the skin opening. The improvements are also embodied in the provision of markings on the skin closure for use in realigning corresponding opposite edges of a skin opening or incision during closing thereof.

19 Claims, 3 Drawing Sheets

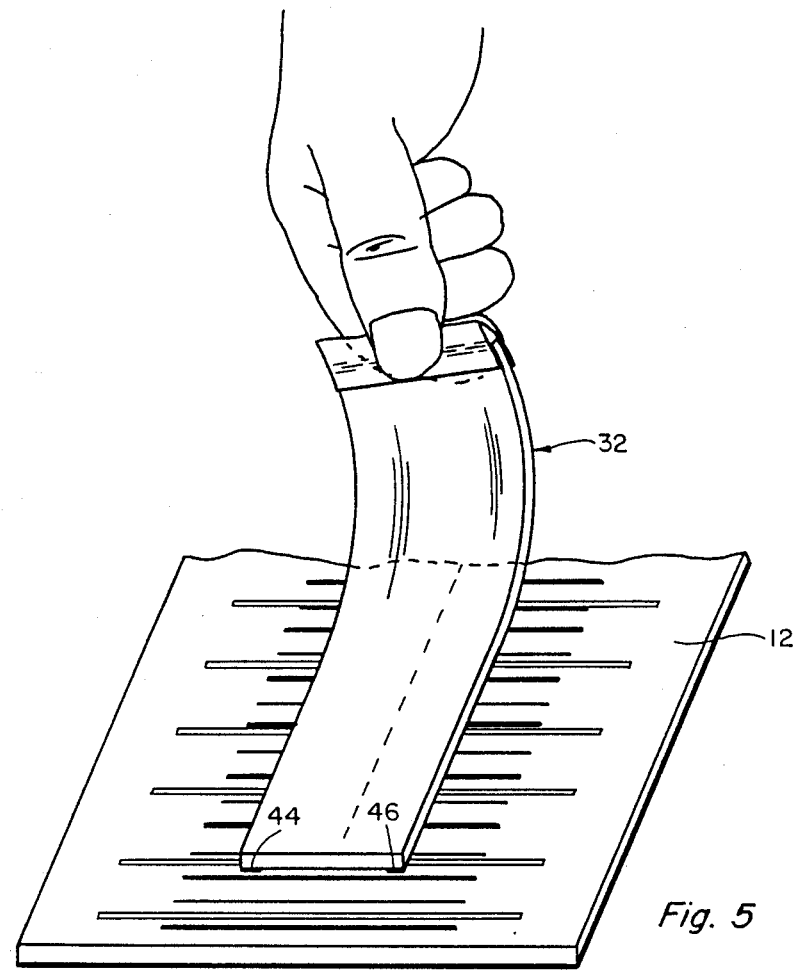
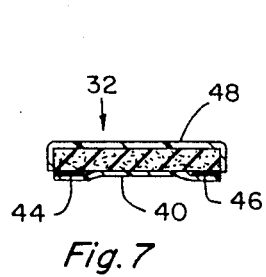
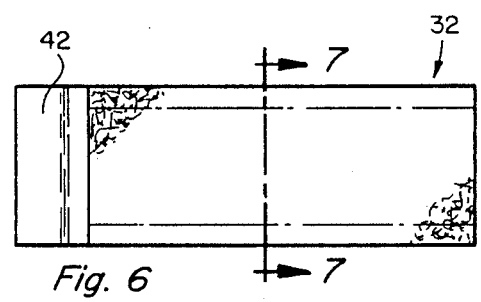
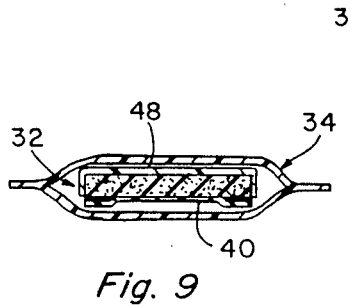
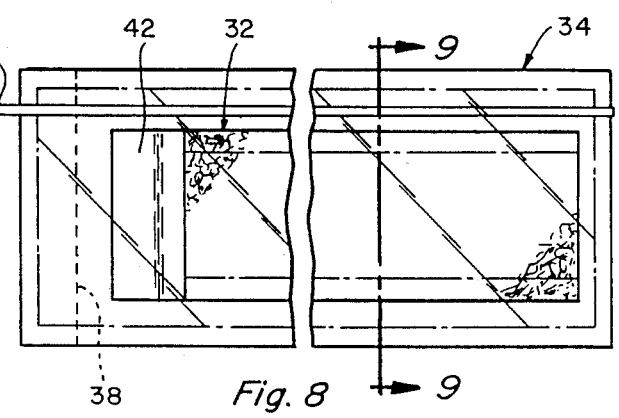

SKIN CLOSURE DEVICES

The present invention represents important improvements over previous skin closure inventions of the applicant as covered by U.S. Pat. Nos. 3,863,640, 3,933,158, 4,114,624 and 4,531,521 and by pending U.S. patent application Ser. No. 742,993, filed June 10, 1985.

The present improvements reside in means for applying medication including applying medication to an incision such as an incision made during surgery or by accident. The subject means are applied after the incision or skin opening has been closed. The idea of the present device is to provide means to maintain a supply of medication adjacent to the closed skin opening or incision in order to reduce the chance for infection and to accelerate the healing process. The subject means enables the surgeon or person closing the skin opening to apply the medication as the last step in the skin closure, and it enables a nurse or other attendent to thereafter continue to apply medication to the skin opening, as needed, and without having to reopen the incision or remove the skin closure means. The present improvements also relate to means to make it possible to more accurately match the sides of a skin opening during closure to facilitate healing and to prevent skin irregularities and keloiding.

It is therefore an object of the present invention to improve the healing prospects and to reduce the chances for infection around and along an incision or skin opening after the opening has been closed.

Another object is to provide improved relatively inexpensive means to medicate the edges of a skin opening that has been closed and to maintain a supply of medication therealong.

Another object is to enable medication to be applied to an incision after the surgery has been performed and to facilitate replenishing the supply of medication as needed without reopening the incision or removing the skin closure means.

Another object is to provide more accurate means to close a skin opening or incision.

These and other objects and advantages of the present invention will become apparent after considering the following detailed specification covering preferred embodiments thereof.

BRIEF DESCRIPTION OF THE DRAWINGS

FIG. 5 is a view showing application of a medication strip to the subject skin closure;

FIG. 6 is a top plan view of a medicated strip for use on the present skin closure means;

FIG. 7 is an enlarged cross-sectional view taken on line 7—7 of FIG. 6;

FIG. 8 is a top view of a sterile package with a medication strip such as shown in FIGS. 6 and 7 positioned therein;

FIG. 9 is a cross-sectional view taken on line 9—9 of FIG. 8; and

DETAILED DESCRIPTION OF THE PREFERRED EMBODIMENTS

Figure 1:
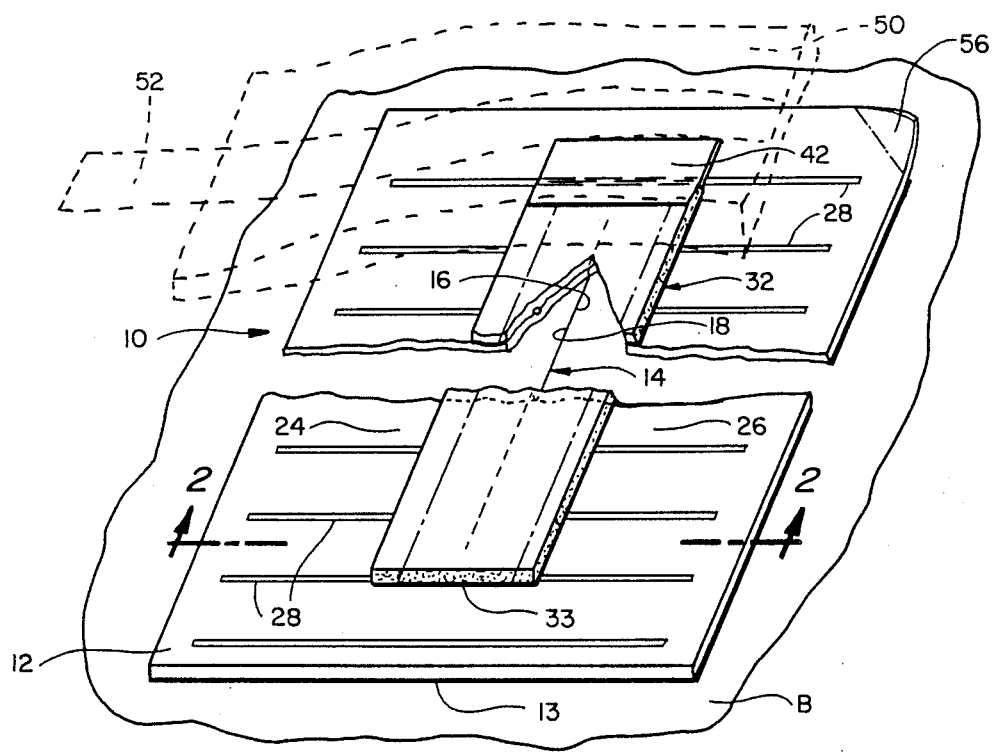
FIG. 1 is a perspective view of a skin closure device, shown closing a skin opening, embodying some of the teachings of the present invention.
Figure 2:
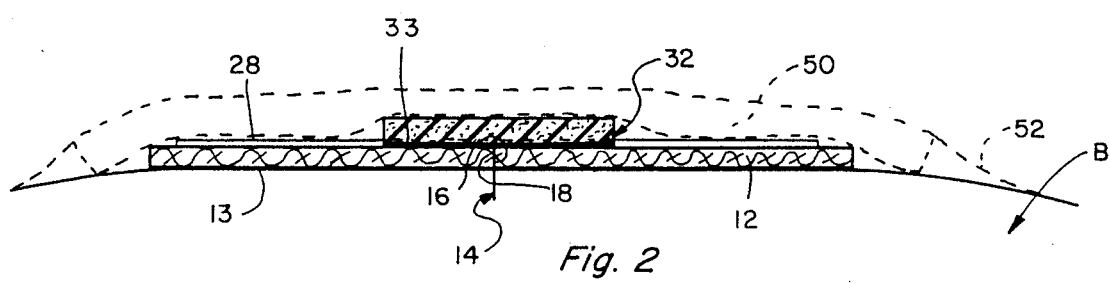
FIG. 2 is an enlarged cross-sectional view taken along line 2—2 of FIG. 1.

Referring to the drawings more particularly by reference numbers, number 10 in FIG. 1 refers to a skin closure device of the type shown in my U.S. Pat. No. 4,531,521 and in pending application Ser. No. 742,993 but modified by incorporating thereon the subject improvements. The skin closure means as shown includes a sheet 12 of material for adhesively attaching by adhesive 13 to the body B of a patient adjacent to and extending along an accidental or surgical skin opening 14, the sheet having adjacent side edges 16 and 18 positioned extending along and closely adjacent to opposite side edges 20 and 22 of the skin opening 14. The sheet 12 may be of one or two piece construction and includes sheet portions 24 and 26 located on opposite sides of the incision 14, which portions are connected together when closing a skin opening by bridging means or members 28 shown as elongated adhesive members that span the skin opening. The well known STERI-STRIPS can be used for this purpose. The members 28 are attached first to the sheet member 12 on one side of the skin opening 14, and thereafter are drawn taught to bring the edges 20 and 22 of the skin opening together and in proper alignment as will be shown before being adhesively attached to the sheet portion on the opposite side of the skin opening.

In the case of a long incision or long skin opening to be closed it may be difficult to keep the sheet portions 24 and 26 of the sheet member 12 in proper orientation or alignment during closure in order to also align the corresponding opposite sides of the skin opening. Because of this it may be desirable, especially if the sheet 12 is applied before the surgeon makes his incision, to provide transverse markings such as markings 30 arranged in a row along or across the sheet, which markings will enable the surgeon to accurately realign the edges 20 and 22 when closing the incision. This is done when the sheet portions 24 and 26 are brought together during the skin closure to enable the surgeon to line up the corresponding markings 30 along opposite sides of the skin opening to bring and maintain corresponding portion of the skin opening or incision together and in accurate alignment. Accurate in this case means reestablishing the alignment of each portion of the opening as it was before the surgery. By doing this it greatly facilitates the healing process and prevents the skin from developing irregularities such as wrinkles or tucks, and it reduces keloiding. This is not as much of a problem where the incision or skin opening is relatively short, but it can be a major problem for long incisions such as occurs in certain types of surgery such as in caesarean sections, abdominal or thoracic surgery, and like procedures.

Once the skin opening or incision has been closed in the manner described using the bridging members 28 to hold the sheet portions on opposite sides of the skin opening together and in abutment, the abutting edges of the sheet portions 24 and 26 will Provide an opportunity therebetween to apply medication to the skin edges along the opening. The application of a continuous supply of medication, such as an antibiotic or disinfectant, an anti-inflamatory drug, an analgesic compound, an angiogenesis or tissue growth factor, or any other compound intended to cause one or more desirable biological effects, in this way can prevent infection from occuring and can aid the healing process. If on the other hand the medication is applied at the conclusion of the skin closure as by daubing or sprinkling the medication onto the skin closure, whether in liquid or powder form, much of the medication will be washed away and be wasted and some will evaporate or be lost by being absorbed in a guaze or other protective cover and will not reach the place where it is needed most and where the healing is taking place.

To overcome this problem the present invention teaches applying adhesively or by other means, a strip, and preferably a sponge like strip 32 of a porous and permeable material. The application of the strip 32 will be by adhesive layer 33 substantially along the length thereof such that the strip will extend along and on top of the skin closure so that there will be a continuous supply of medication seeping or draining between the abutting edges 16 and 18 of the sheet portions 24 and 26 to maintain a sterile and medicated condition along the skin edges. Such a strip is shown in FIGS. 5–7. The strip 32 can be applied at the conclusion of the skin closure operation by the surgeon or by some other person making the closure as shown in FIG. 5.

The medicated strip 32 can be supplied in a sterile condition inside of a sterilized wrapper 34 (FIGS. 8 and 9) which wrapper can have a tear strip 36 or other means such as a line of depressions 38 to make it easy to open.

It is an important feature of the present inventions to have the strip 32 applied to the skin closure rather than directly to the skin because it makes its application more accurate for the purpose intended and it also makes removal easier and less painful. Also, by having the strip 32 formed of a sponge or sponge-like material it can be filled to the extent desired in advance with a liquid or dry powder medication which will drain or seep or can be made to drain or seep into the skin separation. If a liquid medication is used nothing further generally needs to be added except possibly to add more later. However, if a dry powder is used the surgeon and later a nurse or other medical attendant taking care of the patient after the skin closure is completed, can periodically check the skin closure and if necessary apply additional medication or liquid to the strip 32 to further dissolve the powder and extend the medication period or they can apply a new strip.

It is also contemplated that the adhesive side 33 of the strip 32 can be protected until needed by a removable cover layer 40, and it is contemplated that the medicated strip 32 will be removed from the skin closure 10 after it has served its purpose to permit air to more easily reach the area where the healing is taking place. An optional nonadhesive end tab 42 on the strip may also be provided to make it easy to take hold of the strip 32 when removing same. The strip 32 is easy to apply and to remove and while it is applied it will medicate the area especially during the early stages of healing when the most help and protection are needed and when there is the greatest possibility for infection. It is also contemplated to provide spaced adhesive strips 44 and 46 adjacent to opposite edges of the strip 32 rather than having an overall adhesive layer 33 on the side that is attached to the skin closure 10. This will provide a space between adhesive strips 44 and 46 which will be more open for the medication to drain out. The strip 32 can also have an optional impervious cover or other layer 48 applied to its outer exposed surfaces to prevent the medication from escaping except to the area of the skin opening. The cover layer 48 will also reduce waste of the medication by leaking into an absorbent protective gauze or like covering 50 attached to the skin by tape 52 as shown.

For the reasons stated the present invention represents significant and important improvements for use with skin closure devices such as some of those disclosed in applicant's own prior patents and pending application. The present improvements substantially improve the healing process by providing means for more accurately lining up corresponding portions of the skin edges when an incision or skin opening is closed, and it also provides means for medicating and reducing the chances of infection by providing means which extend along the incision after it is closed to provide a continuous supply of medication thereto.

Figure 10:
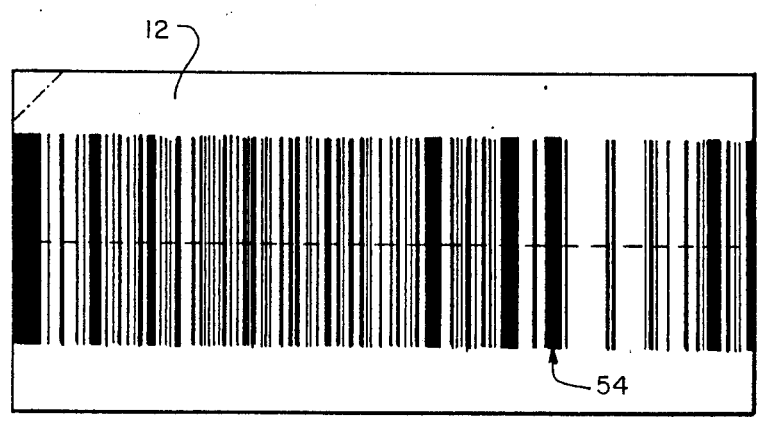
FIG. 10 is a top view of the sheet portion of the subject device showing another pattern of markings formed thereon.
Figure 3:
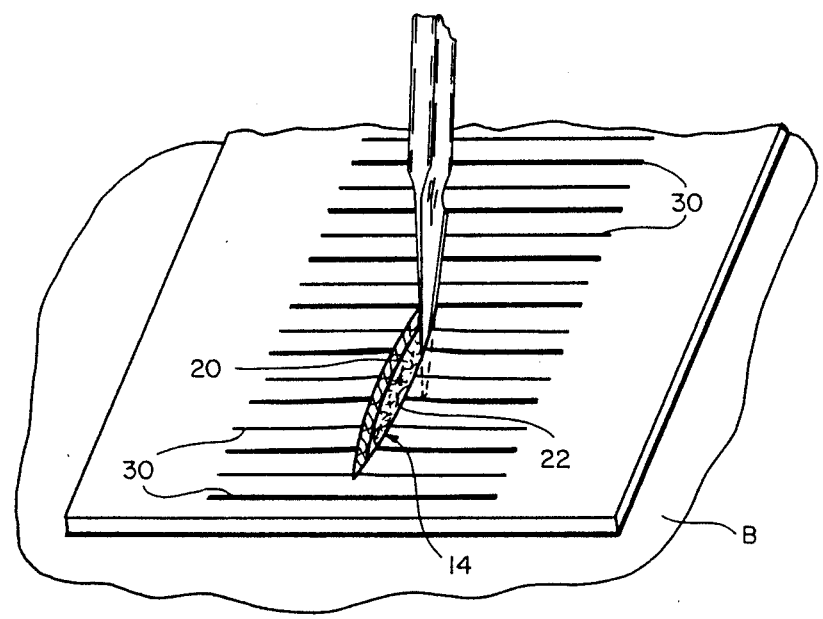
FIG. 3 is an enlarged perspective view showing an incision being made using the subject skin closure means.
Figure 4:
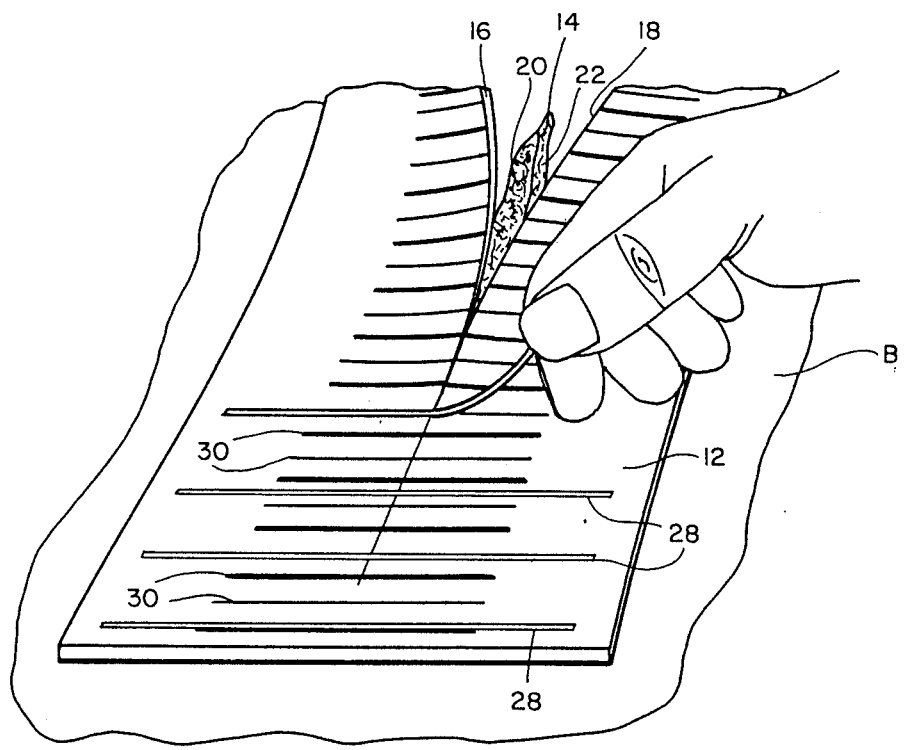
FIG. 4 is an enlarged fragmentary view showing closure of the subject skin closure.

FIG. 10 shows another form of marking 54 for aligning the skin opening. In this case a spectrum of lines in black and white or even in color is used as an aid to alignment. Diagonal or wavy lines or patterns can also be used.

The sheet 12 may also have a tab 56 (FIG. 1) at one corner that is not adhesively attached to the body B to facilitate its removal.

Thus there has been shown and described novel means for use with skin closure devices and novel means for medicating a skin opening after it has been closed in order to improve the healing process and reduce the chance for infection, which improvements fulfill all of the objects and advantages sought therefor. It will be apparent to those skilled in the art, however, that many changes, modifications, variations and other uses and applications for the subject improvements are possible, and all such changes, modifications, variations and other uses and applications which do not depart from the spirit and scope of the invention are deemed to be covered by the invention which is limited only by the claims which follow.

What is claimed is:

1. In a skin closure means formed by a sheet of material adhesively attached to the body adjacent to and extending along a skin opening, said sheet having adjacent side edges positioned to extend along opposite side edges of the skin opening, and means bridging the skin opening for attaching portions of the sheet on opposite sides of the opening in position holding the adjacent side edges of the sheet portions and the attached opposite side edges of the skin opening together, the improvement comprising a member attachable to the skin closure extending along the skin opening and the adjacent portions of the sheet member, said member being formed of a porous and permeable material designed to hold a quantity of a medication substance that will drain between the adjacent sheet side edges to the area around the skin opening and indicator markings applied to the sheet member to provide a means for aligning corresponding portions of the skin opening with each other during skin closure.

2. In the skin closure of claim 1 wherein the indicator markings include a spectrum of markings extending across at least a portion of the sheet.

3. In combination with a skin closure means formed by a sheet of material adhesively attachable to the body adjacent to and extending along a skin opening, said sheet having adjacent side edges positioned to extend along opposite side edges of the skin opening, and adhesive means bridging the skin opening for adhesively attaching to portions of the sheet on opposite sides of the opening in position holding the adjacent side edges of the sheet portions and the attached opposite side edges of the skin opening together and in abutment, the improvement comprising a medication-containing member adhesively attachable to the skin closure extending along the skin opening and spanning the abutting side edges of the adjacent portions of the sheet member and the bridging means, said member being formed of a layer of porous and permeable material enclosed within a layer of impermeable material having a flow channel through one side, wherein said flow channel allows a medication substance to drain between the adjacent side edges of the sheet portions to the area around the skin opening, wherein said medication-containing member is adhesively attached to the sheet of material by means of spaced strips of adhesive material which are positioned between said medication-containing member and the surface of said sheet of material opposite from where said sheet of material is attached to the body.

4. In the skin closure means of claim 3, wherein indicator markings are applied to the sheet member to provide a means for aligning corresponding portions of the skin opening with each other during skin closure.

5. In the skin closure means of claim 4 wherein the distinctive indicator markings include a spectrum of markings extending across at least a portion of the sheet.

6. A medication carrier member in combination with a sheet member having a slit therethrough comprising an elongated strip of relatively porous material intended to hold a quantity of medication therein substantially entirely along the length thereof, and adhesive means on one side of said elongated strip along substantially the length thereof for adhesively attaching the strip to the sheet extending along the slit to drain medication into the slit, wherein said adhesive means are positioned between said medication carrier member and the surface of said sheet of material opposite from where said sheet of material is attached to the body.

7. The medication carrier member of claim 6 including a layer of relatively impervious material on the opposite side of the elongated strip from the attaching means.

8. The medication carrier member of claim 6 including means at one end of the elongated strip forming a nonadhesive tab portion.

9. The medication carrier member of claim 6 wherein the attaching means on one side of the elongated strip include a pair of spaced strips of adhesive extending adjacent opposite edges of the elongated strip.

10. The medication carrier member of claim 6 wherein a liquid medication substance is positioned in the strip of porous material.

11. The medication carrier member of claim 6 wherein a medication substance in dry powder form is positioned in the strip of porous material.

12. The medication carrier member of claim 6 wherein the attaching means along one side of the elongated strip includes a layer of adhesive material and a removable protective layer on said adhesive layer.

13. A medication carrier member in combination with a sheet adhesively attached to the skin, the sheet having a slit closing an injury comprising an elongated strip of a relatively porous material capable of retaining a quantity of medication therein, adhesive means extending substantially entirely along one side of said elongated strip for adhesively attaching the strip to the sheet extending along the sheet slit, wherein said adhesive means are positioned between said medication carrier member and the surface of said sheet of material opposite from where said sheet of material is attached to the body, a removable protective cover over the adhesive means, and a package for retaining the elongated strip in a sterilized condition.

14. The carrier member of claim 13 wherein the medication is applied to the strip in a liquid form.

15. The carrier member of claim 13 wherein the medication is applied to the strip in a powdered form which dissolves when liquid is applied to the strip.

16. The carrier member of claim 13 wherein the package has a tear strip extending thereacross which can be pulled to sever the package for removal of the strip.

17. A skin closure comprising a sheet of material having opposite surfaces, an adhesive applied to one of the surfaces for attaching the sheet to a body of a person at a location where a skin opening is to be closed, said sheet having adjacent side edges positioned to extend along opposite side edges of the skin opening, means bridging the skin opening for attaching to portions of the sheet on opposite sides of the opening in positions to hold the adjacent sheet side edges and the attached side edges of the skin opening together, and means forming a pattern of transversely extending markings on the sheet and not directly on the body at spaced locations therealong, said transversely extending markings providing means for aligning the opposite side edges of the sheet portions and the skin attached thereto during a skin closure operation.

18. The skin closure of claim 17 wherein the transversely extending pattern of markings applied to the sheet include a pattern of markings extending across at least a portion of the sheet whereby part of the pattern of markings is located adjacent each of the adjacent sheet side edges.

19. The skin closure of claim 17 including an elongated strip of relatively porous material intended to hold a quantity of medication therein substantially entirely along the length thereof, and means on one side of said elongated strip along substantially the length thereof for adhesively attaching the strip to the skin closure in position extending along the skin opening.

* * * * *

UNITED STATES PATENT AND TRADEMARK OFFICE
CERTIFICATE OF CORRECTION

PATENT NO. : 4,976,726

DATED : December 11, 1990

INVENTOR(S) : Charles B. Haverstock

It is certified that error appears in the above-identified patent and that said Letters Patent is hereby corrected as shown below:

In the Abstract, line 16 after into, "the" should be --and--.

Column 1, line 42 after "more" the "," should be deleted.

Column 2, line 65, Provide should be --provide--.

Signed and Sealed this

Twenty-eighth Day of April, 1992

Attest:

HARRY F. MANBECK, JR.

Attesting Officer     Commissioner of Patents and Trademarks